United States Patent [19]
Kang et al.

[11] Patent Number: 5,919,579
[45] Date of Patent: Jul. 6, 1999

[54] ORGANIC ELECTROLUMINESCENT DEVICE

[75] Inventors: Wen-Bing Kang, Tokorozawa, Japan; Nu Yu, Oberursel, Germany; Akihiko Tokida, Kawagoe, Japan; Thomas Potrawa, Seelze; Andreas Winterfeldt, Barsinghausen, both of Germany

[73] Assignee: Hoechst Aktiengesellschaft, Frankfurt, Germany

[21] Appl. No.: 08/776,078

[22] PCT Filed: Aug. 7, 1995

[86] PCT No.: PCT/EP95/03128

§ 371 Date: Jan. 17, 1997

§ 102(e) Date: Jan. 17, 1997

[87] PCT Pub. No.: WO96/05267

PCT Pub. Date: Feb. 22, 1996

[30] Foreign Application Priority Data

Aug. 8, 1994 [JP] Japan .................................. 6-185820

[51] Int. Cl.⁶ .................................................. H05B 33/00
[52] U.S. Cl. .......................... 428/690; 428/691; 428/917; 313/504
[58] Field of Search ..................... 428/690, 917; 313/504

[56] References Cited

FOREIGN PATENT DOCUMENTS 0 398 764  11/1990  European Pat. Off. .

OTHER PUBLICATIONS

Database WPI, Sec. Ch, Wk. 9252, Derwent Pub. Ltd., Class E13, AN 92–426615 & JP A 04 320 486 (Mitsubishi Kasei Corp), Nov. 11, 1992.

Database WPI, Sec. Ch, Wk. 9204, Derwent Pub. Ltd., Class E19, AN 92–028265 & JP A 03 274 695 (NEC CORP), Dec. 5, 1991.

*Primary Examiner*—Charles Nold
*Attorney, Agent, or Firm*—Frommer Lawrence & Haug LLP

[57] ABSTRACT

An organic electroluminescent device comprising an anode, an organic hole transport layer, an organic emission layer and a cathode layered in this order on a substrate, or, optionally, comprising an additional electron transport layer between the organic emission layer and the cathode, wherein the organic emission layer comprises a naphthalimide derivative represented by formula (1) wherein $R^1$ is a hydrogen atom, a straight chain or branched chain alkyl group having from 1 to 16 carbon atoms, an aryl group which may have substituents or an aralkyl group which may have substituents, and $R^2$, $R^3$, $R^4$ are special substituents.

4 Claims, 2 Drawing Sheets

ORGANIC ELECTROLUMINESCENT DEVICE

This application is a §371 of PCT/EP95/03128, filed Aug. 7, 1995, based on Japanese Application No. 185820/94, filed Aug. 8, 1994.

This invention relates to an emission device by utilizing electroluminescence of an emitting element which emits light by injection of an electric current wherein the emission device is provided with an emission layer wherein the emitting elements are formed into layers. More specifically, it relates to an organic electroluminescent device (hereinafter referred to as "organic EL device") in which the emission layer is composed of an organic compound as an emitting element.

Hithertofore, organic EL devices having various structures have been proposed. For example, a two-layer type structure wherein a thin film of a fluorescent material 2 as an emission layer and a hole transport layer 3, each comprising an organic compound and being layered on each other, are arranged between a metal cathode 1 and a transparent anode 4, as shown in FIG. 1; and a three-layer type structure wherein an electron transport layer 6 comprising an organic compound, an emission layer 2 and a hole transport layer 3 are layered between a metal cathode 1 and a transparent anode 4 are known. In the above devices, the hole transport layer 3 has the function of easily injecting positive holes from the anode and the function of blocking electrons; and the electron transport layer 6 has the function of easily injecting the electrons from the cathode and the function of blocking holes.

In these organic electroluminescent devices, ITO is mainly used for the transparent electrode 4, and a film thereof is formed on a glass substrate 5. By recombination of on electron injected from the metal cathode 1 and a hole injected into the emission layer from the anode 4, light radiated in the process of radiative decay of the produced exciton is emitted through a transparent anode and a transparent glass substrate.

Detailed explanation of organic electroluminescent devices are described, for example, in the following literature references:

(1) "Organic EL Device Development Strategy", compiled by Next Generation Display Device Research Association, Science Forum (published 1992)

(2) "Electroluminescent Materials, Devices, and Large-Screen Displays", SPIE Proceedings Vol. 1910 (1993), E. M. Conwell and M. R. Miller However, in the conventional organic EL devices, the stability of light-emission is not necessarily considered sufficiently satisfactory, and organic EL devices which emit light more stably are desired. Under such circumstances, the present inventors extensively studied the development of organic EL devices having excellent characteristics, and, as a result, found that an organic EL device having an improved stability can be obtained by using a specific naphthalimide derivative, and, based on this finding, completed the present invention. An object of the present invention is to provide an organic EL device which stably emits at high luminance.

The organic EL device according to the present invention is characterized in that, in the organic EL device comprising an organic compound, the emission layer comprises a naphthalimide derivative represented by the formula (1):

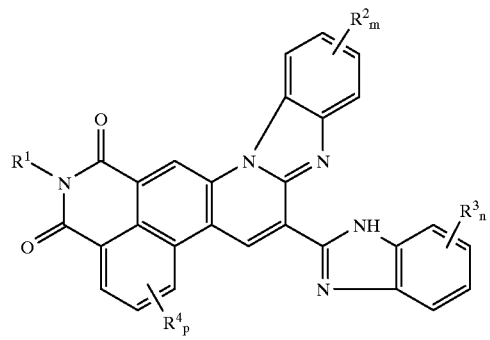

(1)

wherein $R^1$ represents a hydrogen atom, a straight chain or branched chain alkyl group having from 1 to 16 carbon atoms, an aryl group, preferably having from 4 to 10 carbon atoms, which may have one or more substituents or an aralkyl group, preferably having from 5 to 22 carbon atoms, which may have one or more substituents;

$R^2$, $R^3$, $R^4$ independently of each other, represent an alkyl, alkoxy or ester group, each having from 1 to 16 carbon atoms, an aryl- or aryloxy group, having from 4 to 10 carbon atoms, which may have one or more substituents, —CN, —$CF_3$, F or $NR^5R^6$, wherein $R^5$, $R^6$ independently of each other represent an alkyl group, having from 1 to 16 carbon atoms, or an aryl group, having from 4 to 10 carbon atoms, which may have one or more substituents;

m, n, p are 0, 1, 2 or 3, preferably 0, 1 or 2, most preferably 0.

Preferably, $R^2$ and $R^3$ have the same meaning.

In the above-described formula (1), when $R^1$ represents a straight chain or branched alkyl group having from 1 to 16 carbon atoms, an alkyl group having from 1 to 6 carbon atoms, for example, a methyl group, an ethyl group and a t-butyl group, are preferred. When $R^1$ is an aryl group which may have a substituent, examples of preferred groups include the phenyl group, the 4-t-butylphenyl group and the naphthyl group. Further, when $R^1$ is an aralkyl group, preferred groups include the benzyl group and the phenethyl group.

Specific examples of compounds which can be preferably used in the present invention are shown below.

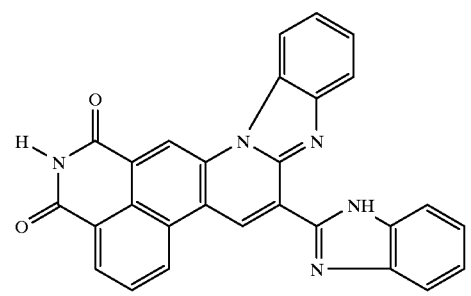
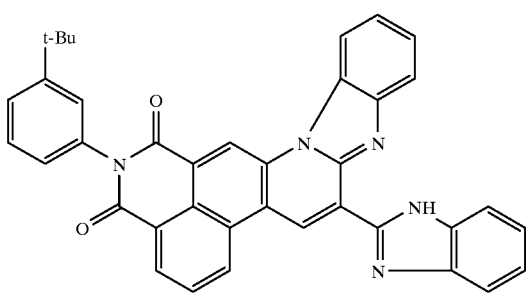
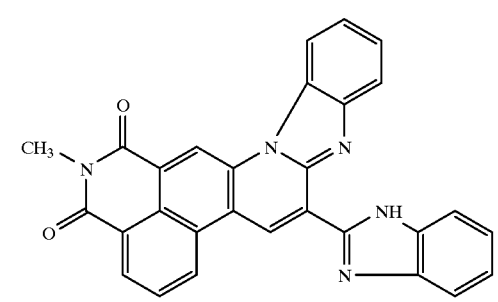
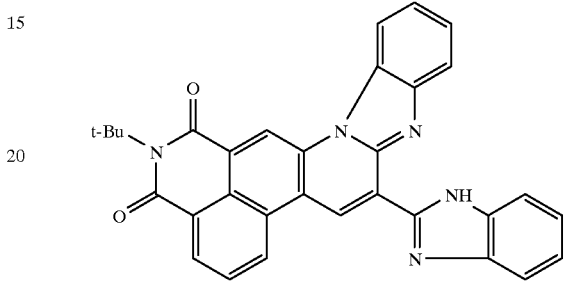
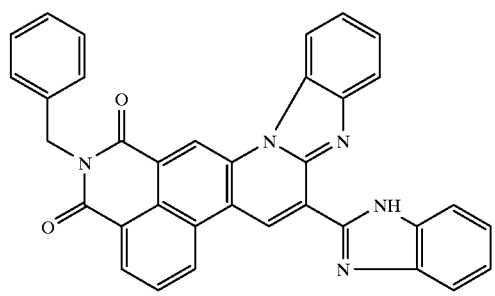
The naphthalimide derivatives of the present invention can be prepared according to the following reaction scheme:
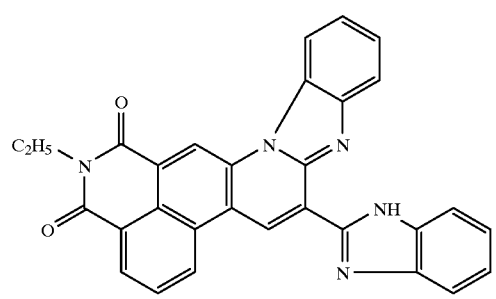

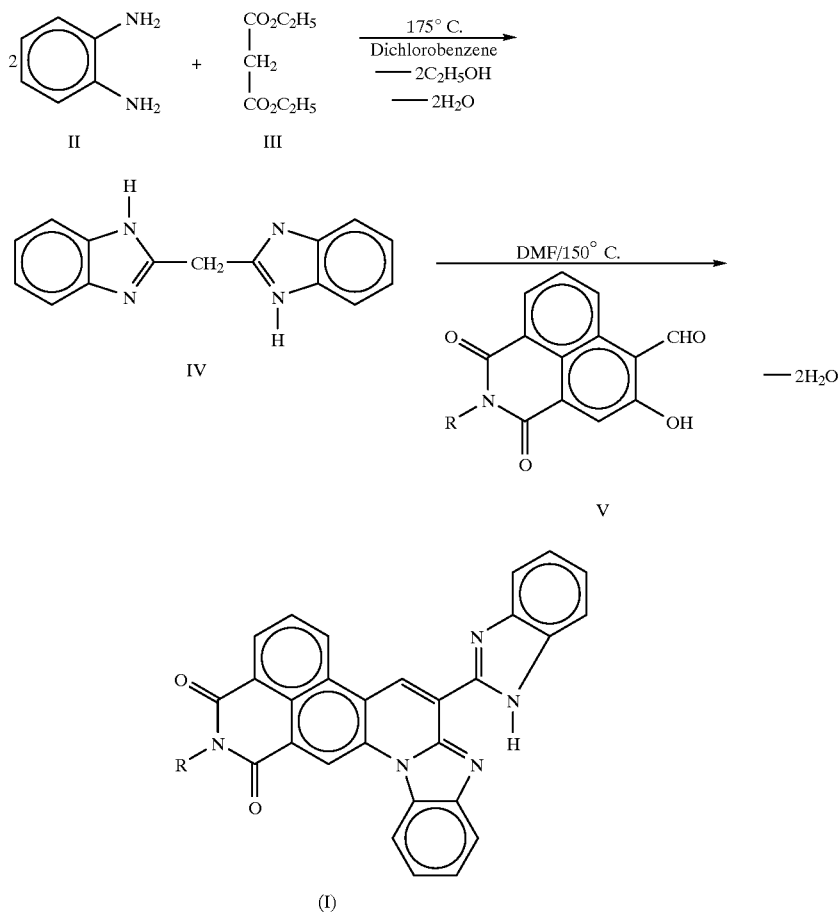

o-Phenylenediamine (II), which can optionally be substituted, is reacted with malonic ester (III) in dichlorobenzene at elevated temperatures to yield the bis-benzimidazol-2-yl methane derivative (IV). (IV) ist further reacted with an N-substituted derivative of 3-hydroxy-4-formyl-naphthalimide (V) in DMF at elevated temperatures to obtain compounds of the formula (I).

The synthesis ov various derivatives of (V) is, for example, described in U.S. Pat. No. 4,002,630, which is incorporated herein by reference.

For instance if R in formula (V) is —CH$_3$, the compound can be prepared according to the following procedure:

227.0 parts of 3-hydroxynaphthalic acid N-methylimide, prepared by condensation of 3-hydroxynaphthalic acid anhydride with stoechiometric amounts of monomethylamine in water at 120° C., 140.0 parts of hexamethylenetetramine and 30.0 parts of paraformaldehyde were successively introduced into 3000 parts of glacial acetic acid; the mixture was stirred for 5 hours at 100° C.

150.0 parts of a 95% sulfuric acid diluted with 90.0 parts of water, were added dropwise within 30 minutes. The reaction mixture was stirred for 1 hour, and subsequently 150.0 parts of a 95% b.w. sulfuric acid were added, whereby a clear solution was obtained. The reaction was brought to an end while stirring for 1 hours at 100° C. The solution resulting from the reaction was cooled to 20° C., the precipitate was sepatated by filtration, washed with water until neutral and dried.

200.0 parts (88.8% of the theory) of aldehyde were obtained.

The naphthalimide derivatives of the present invention can be used alone, or as a mixture thereof with other compounds of the present invention and compounds which are known as light-emitting materials, or as a dispersion in a polymer, for example, polyvinylcarbazole, polymethacrylate, polyester and polyimide, preferably a hole transport polymer such as polyvinylcarbazole.

Examples of compounds used in the present invention are shown hereinafter, but the scope of the present invention is not limited thereto.

EXAMPLE

Figure 1:
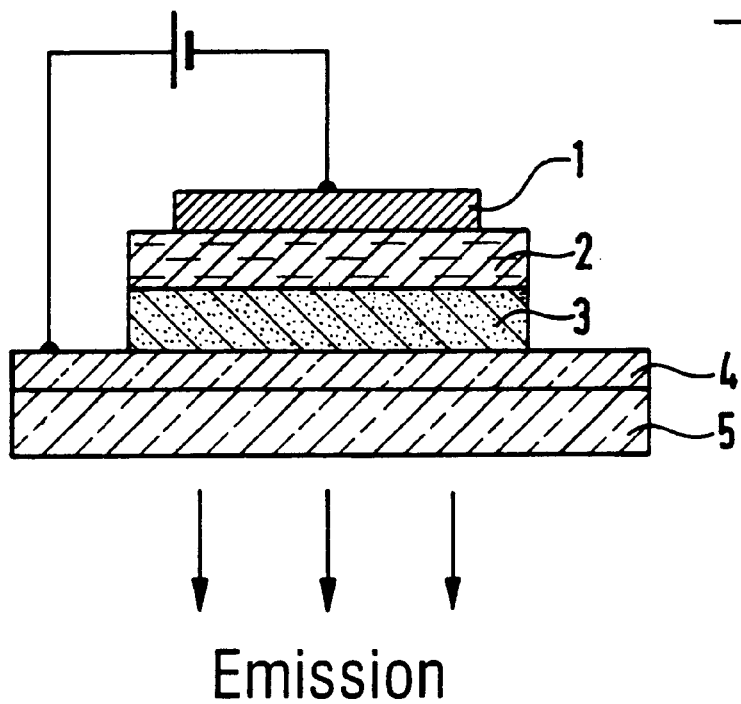
FIG. 1 depicts a cross-sectional drawing showing an example of the organic EL device in which an anode, a hole transport layer, an emission layer and a cathode are layered in this order.
Figure 2:
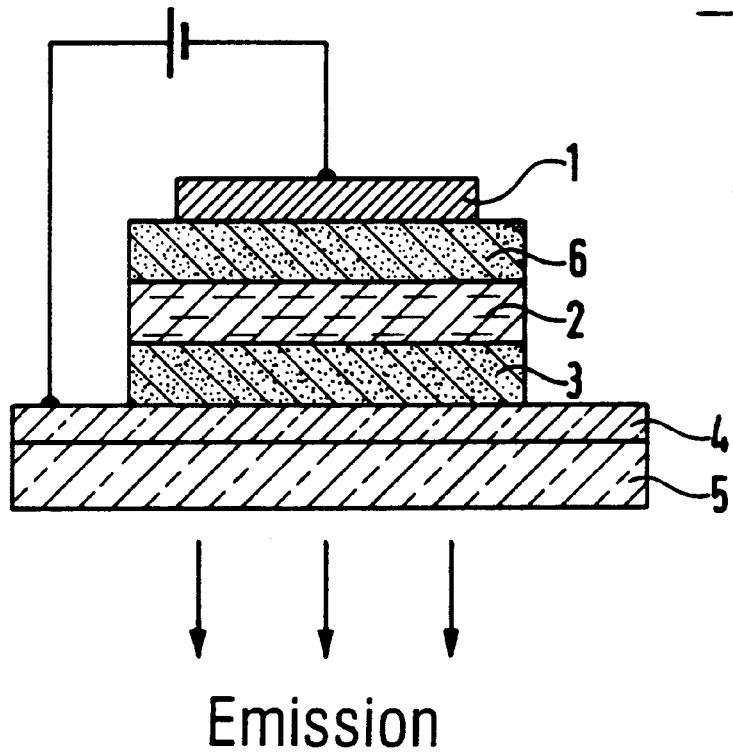
FIG. 2 depicts a cross-sectional drawing showing an example of the organic EL device in which an anode, a hole transport layer, an emission layer, an electron transport layer and a cathode are layered in this order.

An example according to the present invention is illustrated below by referring to the drawings. As shown in FIG. 1, the organic EL device of this example has a structure wherein an anode 4, a hole transport layer 3 comprising an organic compound, an electron transport emission layer 2 comprising a naphthalimide derivative of the present invention and a metal cathode 1 are layered in order on a glass substrate 5 (an ITO glass substrate). Further, as shown in FIG. 2, in addition to the above construction, it may have a structure wherein an electron transport layer 6 comprising an organic compound is layered between the emission layer 2 and the metal cathode 1 on the glass substrate 5.

The hole transport compound which can be used in the hole transport layer 3 in the above-described device structure is a compound containing a tertiary amine which has at least one bonded aromatic ring, or other low molecular weight compounds or polymeric compounds having a hole transporting property and, for example, diamines represented by formula (3) (hereinafter referred to as TPD) are preferably used. In addition, compounds which are generally known as hole transport materials can be used alone or as a mixture thereof. Typical examples of the hole transport compounds include tetraphenylbiphenylenediamine, pyrazoline, polyvinylcarbazole and polysilane.

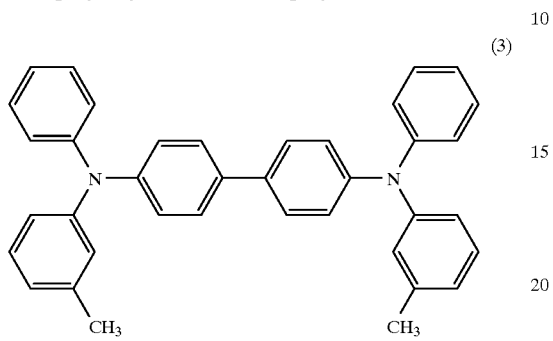

(3)

The light emitting material used in the electron transport emission layer 2 of the device structure shown in FIG. 1 is the naphthalimide derivative having an electron transporting property according to the present invention.

Also, a device structure shown in FIG. 2 is particularly preferred for naphthalimide derivatives of the present invention having a relatively low electron transporting property. In this case, the compound used in the electron transport layer 6 can be a conventionally known electron transporting material. For example, t-Bu-PBD represented by formula (4) or Alq3 (Tris(8-hydroxyquinoline) aluminum) can be used.

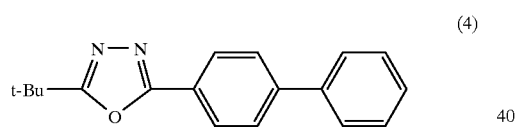

(4)

Materials for the anode used in the present invention are preferably those having a work function as high as possible, and, for example, nickel, gold, platinum, selenium, iridium, or an alloy thereof, or tin oxide, ITO or copper iodide, the latter two being preferred. Also, an electroconductive polymer such as polyphenylene sulfide or polyaniline can be used.

On the other hand, materials for the cathode which can be used are those having a low work function such as silver, lead, tin, magnesium, aluminum, calcium, indium, chromium, lithium or an alloy thereof. Further, of the materials used as the anode and cathode, at least one of these electrodes is preferably that transmit 50% or more of the light in the region of emission wavelength of the device. The transparent substrate which can be used in the present invention includes glass and plastic film, etc.

Figure 3:
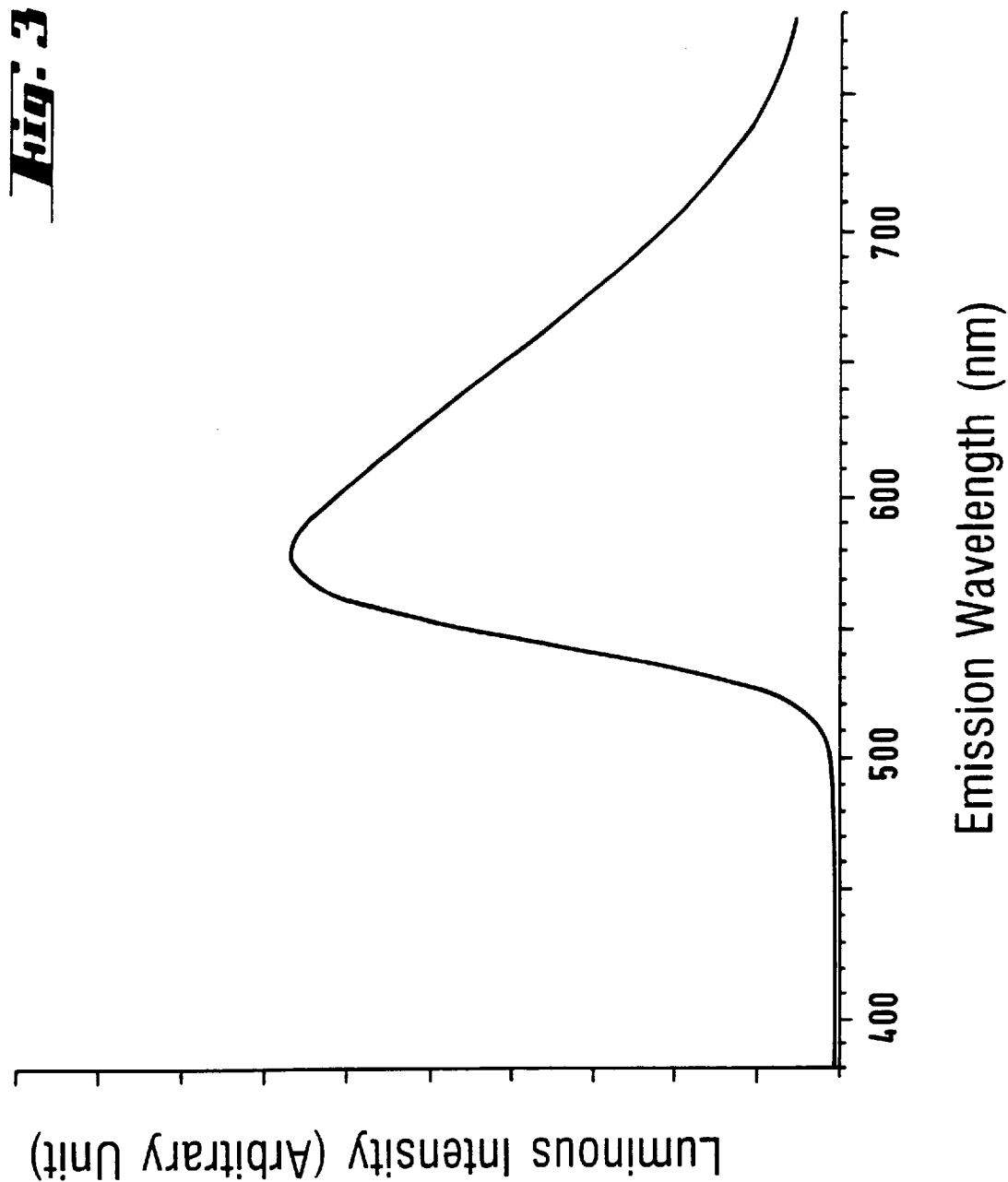
FIG. 3 depicts a graph showing the light emission spectrum of the organic EL device of the present invention.

In an embodiment, a TPD in a 50 nm thickness and then a naphthalimide derivative represented by the formula (5) below in a 50 nm thickness were layered in a vacuum of $5 \times 10^{-5}$ torr at a rate of 3 to 7 Å/sec by the resistance heating method on a well-rinsed ITO glass substrate. Further, an electrode of a silver-magnesium alloy of 2 mm×2 mm in a 250 nm thickness was layered by vapor deposition through a mask of 2 mm×2 mm at rates of 1 Å/sec of silver and 9 Å/sec of magnesium in a vacuum of $6 \times 10^{-6}$ torr by the resistance heating method. Negative and positive electric field were applied to the ITO side and the aluminum side of the device, respectively, and a luminous intensity from the ITO glass substrate of the device was measured and, as a result, stable orange electroluminescent emission having a luminance of 14 $Cd/m^2$ was observed at a voltage of 10V and an electric current density of 100 $mA/cm^2$. The light emission spectrum from the above-described device is shown in FIG. 3.

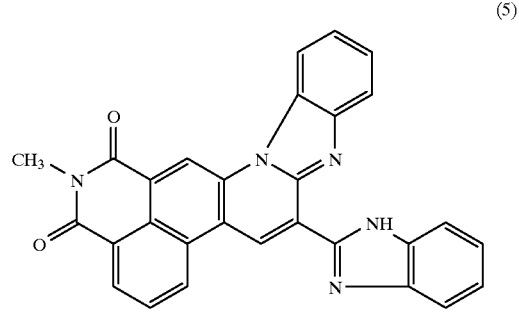

(5)

According to the present invention, an organic EL device having a good stability can be obtained by using a thin film of the naphthalimide derivative.

What is claimed is:

1. An organic electroluminescent device wherein an anode, a hole transport layer comprising an organic compound, an emission layer comprising an organic compound, an electron transport layer, and a cathode are layered in this order, characterized in that said emission layer contains a naphthalimide derivative represented by the formula (1):

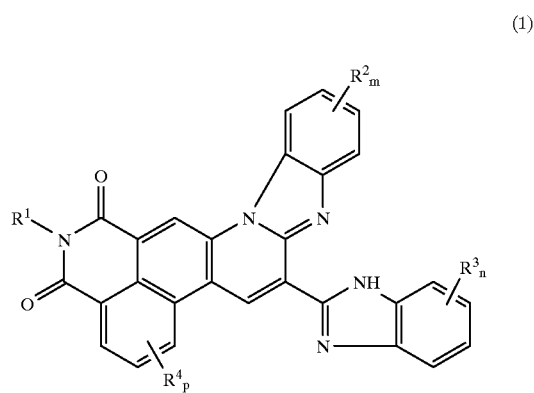

(1)

wherein $R^1$ represents a hydrogen atom, a straight chain or branched chain alkyl group having from 1 to 16 carbon atoms, an aryl group, which may have one or more substituent or an aralkyl group, which may have one or more substituents;

$R^2$, $R^3$, $R^4$ independently of each other, represent an alkyl, alkoxy or ester group, each having from 1 to 16 carbon atoms, an aryl- or aryloxy group, having from 4 to 10 carbon atoms, which may have one or more substituents, —CN, —$CF_3$, —F or —$NR^5R^6$, wherein $R^5$, $R^6$ independently of each other represent an alkyl group, having from 1 to 16 carbon atoms, or an aryl group, having from 4 to 10 carbon atoms, which may have one or more substituents;

m, n, p are 0, 1, 2 or 3.

2. An organic electroluminescent device wherein an anode, a hole transport layer comprising an organic compound, an emission layer comprising an organic compound, and a cathode are layered in this order, characterized in that said emission layer contains a naphthalimide derivative represented by the formula (1):

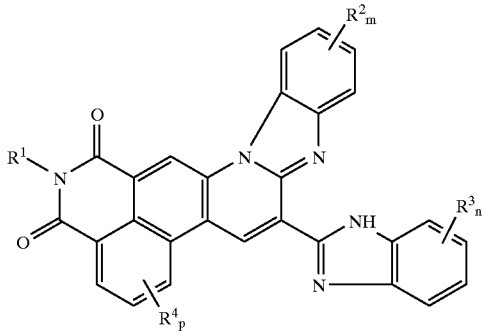

(1)

wherein $R^1$ represents a hydrogen atom, a straight chain or branched chain alkyl group having from 1 to 16 carbon atoms, an aryl group, which may have one or more substituent or an aralkyl group, which may have one or more substituents;

$R^2$, $R^3$, $R^4$ independently of each other, represent an alkyl, alkoxy or ester group, each having from 1 to 16 carbon atoms, an aryl- or aryloxy group, having from 4 to 10 carbon atoms, which may have one or more substituents, —CN, —$CF_3$, —F or —$NR^5R^6$, wherein $R^5$, $R^6$ independently of each other represent an alkyl group, having from 1 to 16 carbon atoms, or an aryl group, having from 4 to 10 carbon atoms, which may have one or more substituents;

m, n, p are 0, 1, 2 or 3.

3. The organic electroluminescent device as claimed in claim 1, wherein m, n, p in the formula (1) are 0.

4. The electroluminescent device as claimed in claim 2, wherein m, n, p in the formula (1) are 0.

* * * * *